US012508373B2

(12) United States Patent
Peruzzo et al.

(10) Patent No.: US 12,508,373 B2
(45) Date of Patent: Dec. 30, 2025

(54) SAFETY DEVICE FOR PREVENTING NEEDLE STICK INJURY WITH A NEEDLE OF A MEDICAL INJECTION DEVICE

(71) Applicant: Becton, Dickinson and Company, Franklin Lakes, NJ (US)

(72) Inventors: Gregory Peruzzo, Prunieres (FR); Franck Carrel, Saint Jean de Vaulx (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 580 days.

(21) Appl. No.: 18/012,456

(22) PCT Filed: Jun. 16, 2021

(86) PCT No.: PCT/IB2021/055324
§ 371 (c)(1),
(2) Date: Dec. 22, 2022

(87) PCT Pub. No.: WO2021/260500
PCT Pub. Date: Dec. 30, 2021

(65) Prior Publication Data

US 2023/0338668 A1 Oct. 26, 2023

(30) Foreign Application Priority Data

Jun. 23, 2020 (EP) .................................... 20181699

(51) Int. Cl.
*A61M 5/32* (2006.01)
*A61M 5/34* (2006.01)

(52) U.S. Cl.
CPC .......... *A61M 5/3216* (2013.01); *A61M 5/343* (2013.01); *A61M 5/3202* (2013.01); *A61M 5/3213* (2013.01)

(58) Field of Classification Search
CPC .. A61M 5/3216; A61M 5/343; A61M 5/3202; A61M 5/3213
See application file for complete search history.

(56) References Cited

U.S. PATENT DOCUMENTS

| | | | |
|---|---|---|---|
| 5,405,332 | A | 4/1995 | Opalek |
| 10,569,029 | B2 | 2/2020 | Carrel |

(Continued)

FOREIGN PATENT DOCUMENTS

| | | | |
|---|---|---|---|
| CN | 101541361 | A | 9/2009 |
| CN | 108112236 | A | 6/2018 |
| CN | 111093740 | A | 5/2020 |

*Primary Examiner* — Tasnim Mehjabin Ahmed
(74) *Attorney, Agent, or Firm* — The Webb Law Firm

(57) ABSTRACT

A safety device includes a ring configured to be attached to a distal tip of a medical injection device and a protective shield movably coupled to the ring and configured to adopt a storage position covering the needle tip, an operative position uncovering the needle tip, and a safety position covering the needle tip A protective cap is mounted on the ring to cover the needle tip, and can be separated from the ring prior to use of the device. A retaining system includes a first retaining portion on the protective shield and a second retaining portion on the protective cap, with the first and second retaining portions cooperating in the storage position to prevent the protective shield from moving to its operative position. A releasing system releases the retaining system and is configured to be activated by a manual inward pressure exerted on the protective cap.

18 Claims, 5 Drawing Sheets

(56) References Cited

U.S. PATENT DOCUMENTS

| | | | | |
|---|---|---|---|---|
| 11,413,400 | B2 | 8/2022 | Carrel et al. | |
| 2002/0091360 | A1 * | 7/2002 | Peters, III | A61M 5/3216 128/919 |
| 2003/0078548 | A1 * | 4/2003 | Kobayashi | A61M 5/3216 604/263 |
| 2009/0270672 | A1 | 10/2009 | Fago | |
| 2012/0191048 | A1 | 7/2012 | Eaton | |
| 2020/0147320 | A1 | 5/2020 | Carrel | |

* cited by examiner

SAFETY DEVICE FOR PREVENTING NEEDLE STICK INJURY WITH A NEEDLE OF A MEDICAL INJECTION DEVICE

CROSS-REFERENCE TO RELATED APPLICATIONS

This application is the United States national phase of International Application No. PCT/IB2021/055324 filed Jun. 16, 2021, and claims priority to European Patent Application No. 20181699.8 filed Jun. 23, 2020, the disclosures of which are hereby incorporated by reference in their entirety.

BACKGROUND OF THE DISCLOSURE

Field of the Disclosure

The disclosure relates to a safety device for preventing needle stick injury with a needle of a medical injection device. The disclosure also relates to a safety assembly comprising such a safety device and a medical injection device.

Description of Related Art

Medical devices provided with sharp pointed needles are of daily practice among the medical community in order to perform injections or to take samples into or from muscles, veins or arteries. They can be injection devices such as syringes, pen-injectors, catheters or blood collection devices. Sharp pointed needles present an inherent risk of needle stick injury for the medical staff and the patients and are thus usually provided with a needle cap covering the needle before use. This cap not only preserves the needle from contamination but also from undesired contacts or punctures that could occur during transport and delivery by the medical staff. Such a cap needs to be removed immediately before use of the medical device.

Replacing the needle cap onto the needle after use is strictly prohibited as it is regarded as a major cause of accident and contamination for the medical staff. Indeed, the whole medical device or at least the used needle should be disposed after use in an appropriate needle collector. However, a risk of needle stick injury still exists as the medical staff handles the bare, contaminated needles before disposal.

Safety devices have thus been designed to prevent needle stick injury with the needle of such medical devices after use i.e. between the end of the injection or collection and the proper disposal of the device. Usually, such safety devices are designed to be locked automatically or manually on at least the needle point when the medical act is finished.

One type of such a safety device includes:

- a protective cap which is mounted on the medical injection device in order to cover the needle in a storage position, and which is to be separated from the medical injection device before use;
- and a protective shield movably coupled to the medical injection device so that the protective shield can adopt a storage position in which the needle is covered, an operative position wherein the needle tip is uncovered, and ultimately a safety position wherein the protective shield covers the needle tip again.

With this type of safety devices, it is of paramount importance to prevent the protective shield in its storage position from unintentionally moving towards its operative position, to ensure the safety of the medical staff and the patients.

For that purpose, several solutions have been provided which include a retaining system that maintains the protective shield in its storage position. However, the known retaining systems may not be fully satisfactory. In particular, they may require a fairly high force from the user to be overcome, to allow the protective shield to move towards its operative position when appropriate.

SUMMARY OF THE DISCLOSURE

An object of the disclosure is to provide an improved safety device. In particular, the disclosure aims at providing a safety device which is easier to operate without impairing safety.

For that purpose, according to a first aspect, the disclosure concerns a safety device for preventing needle stick injury with a needle extending from a distal tip of a medical injection device, the safety device comprising:

- a ring configured to be attached to the distal tip of the medical injection device;
- a protective shield movably coupled to the ring, the protective shield being configured to adopt successively a storage position wherein the protective shield covers the needle tip, an operative position wherein the protective shield uncovers the needle tip and a safety position wherein the protective shield covers the needle tip;
- a protective cap which is mounted on the ring in a storage position so as to cover at least the needle tip, and which can be separated from the ring prior to the use of the medical injection device;
- a retaining system comprising a first retaining portion arranged on the protective shield and a second retaining portion arranged on the protective cap, wherein the first and second retaining portions cooperate in the storage position to prevent the protective shield from moving to its operative position;
- and, further, a releasing system for releasing the retaining system, the releasing system being configured to be activated by a manual inward pressure exerted on the protective cap.

Thus, in the safety device of the disclosure, owing to the retaining system, the protective shield is prevented from unintentionally moving to its operative position. However, when appropriate, i.e. typically immediately before use, a user can release the retaining system to allow the protective shield to move to its operative position, which allows the use of the medical injection device.

Moreover, the way the releasing system is activated has significant advantages.

Pressing the protective cap inwardly is a movement that can be easily performed by almost any user, without requiring a significant effort, and without the risk that the fingers slip on the safety device.

Besides, an inward pressure on the protective cap is unlikely to occur accidentally, for example following an impact from a surrounding element. In case the releasing system and retaining system are arranged on opposite sides of the safety device, it can typically be activated by a user pressing the safety device between his thumbs. Such a movement is even safer in terms of unintentional activation.

Furthermore, such a pressing movement may be performed at the same time as the gripping of the protective cap in order to separate it from the ring. In other words, activating the releasing system generally does not imply successively placing the fingers at various locations on the safety device, which would not be convenient. However, the pressing movement requests an inward force whereas removing the protective cap generally requires a force oriented differently, for example a distally pulling movement. This has two significant consequences. On the one hand, although these two movements can be carried out simultaneously, the need of two distinct movements improves safety by making unintentional activation of the releasing system very unlikely. On the other hand, as these two movements are distinct, each one can require an effort which is not too high, as compared to a design in which activating the releasing system would result from the same movement as removing the protective cap, which could require a higher effort.

The structure of the disclosure further greatly simplifies the design and manufacturing of the safety device, especially in terms of chain of dimensions. Indeed, one and the same piece of the device can be both a part of the retaining system and a part on which the releasing system acts. Assembling the protective shield is easy as it can be performed in a single step; a single one-direction movement is required to mount the protective shield onto the other parts of the safety device.

The releasing system can be arranged on the protective cap.

In an embodiment, in the storage position, the releasing system substantially faces at least a part of the retaining system in the radial direction.

In the storage position, the releasing system may be in contact with or in close proximity to at least a part of the retaining system. As a result, there is no need to make a movement over a large distance to begin the releasing process. However, the first and second retaining portions may be configured to cooperate over a range of said movement which is not too small, to avoid accidental release of the retaining system.

The releasing system may preferably be configured to directly release the retaining system when activated. In other words, with such an embodiment, releasing the retaining system would not require another intermediate member.

In an embodiment, the protective cap comprises a substantially tubular body having a distal radial opening and the protective shield has a distal arm which, in the storage position, is housed in or radially faces the distal radial opening of the protective cap. The first retaining portion may be arranged on at least one of the two longitudinal sides of the distal arm of the protective shield and the second retaining portion may be arranged on a portion of the substantially tubular body peripheral wall adjacent the distal radial opening.

The retaining system and/or the releasing system may comprise at least one element which is configured to be elastically moved, deflected or deformed from a first state, in which the protective shield is maintained in the storage position, towards a second state, in which the protective shield is free to move towards its operative position.

The protective shield can comprise at least one leg extending towards the inside of the safety device, the leg having a protrusion which extends outwardly and which has an abutment face forming the first retaining portion. Said leg preferably extends orthogonally to the safety device axis. In an embodiment, there are provided two legs, arranged opposite to one another.

The protective cap can comprise at least one cavity which opens at least towards the inside of the safety device, one face of said cavity being a shoulder forming the second retaining portion.

The cavity can further form an abutment for axially retaining the leg, i.e. for preventing a relative axial movement between the protective cap and the protective shield. In an embodiment wherein pulling the protective cap distally away from the medical device automatically entails a movement of the protective shield towards its operative position, such a disposition would therefore prevent unintentional movement of the protective shield towards its operative position.

The cavity can extend through the protective cap peripheral wall. In other words, the cavity can open both towards the inside and towards the outside of the safety device.

The leg of the protective shield is configured to be elastically moved, deflected or deformed towards the inside of the safety device upon activation of the releasing system, to disengage from the shoulder of the protective cap.

In an embodiment, the releasing system comprises at least one trigger which is housed in a window arranged in a peripheral wall of the protective cap, the trigger being hingedly connected to at least one edge of the window and being configured to be elastically moved, deflected or deformed towards the inside of the safety device by a manual inward pressure exerted on said trigger.

The trigger may have a H shape with a central rod on which a manual inward pressure can be exerted and two branches on either part of the central rod, each branch being adjacent an edge of the window and hingedly connected to said edge. Preferably, the central rod extends parallel to the safety device axis, i.e. orthogonally to the leg of the protective shield. This ensures that there will be a contact between the central rod and the leg, to cause the retaining system to be released, and involves less dimensioning constraints regarding the relative position of the central rod and the leg to that end.

The trigger can be made as a single piece with the protective cap. A portion of reduced thickness can form a hinge between the trigger and the window edge.

The cavity may further open into the window.

The window may be arranged in an inwardly recessed portion of the peripheral wall of the protective cap, in order to avoid unintentional pressing movement on the trigger.

The recessed portion has an inner face and an outer face, which can both be substantially flat.

The trigger may have a projection which extends outwardly from the recessed portion outer face but not beyond a cylindrical envelope of the protective cap, in the radial direction. As a result, access to the trigger is made easier, as it extends outwardly from the window, but not too easy in order to prevent unintentional triggering of the releasing system.

Alternatively, or in addition, the trigger may have an inner face which is substantially level with the recessed portion inner face. Thus, the trigger does not extend inwardly when it is in the first state (i.e. a state in which the protective shield is maintained in the storage position), but only when a user wants to activate the releasing system.

The shoulder—namely one face of said cavity which forms the second retaining portion—may project inwardly from the recessed portion inner face. As a result, the protrusion can have an activation face very close to the recessed portion inner face, i.e. to the trigger inner face.

In an embodiment, the ring has a first hinge portion and the protective shield has a second hinge portion pivotally coupled to the first hinge portion, whereby the movement of the protective shield from its storage position to its operative position is a pivoting movement.

The protective cap and the protective shield may have cooperating actuation surfaces configured so that a distal movement of the protective cap away from the ring automatically entails a movement of the protective shield from its storage position to its operative position. With the ring and the protective shield being pivotally connected, the actuation surfaces can be cam surfaces.

According to a second aspect, the disclosure relates to a safety assembly, comprising:

- a medical injection device comprising a barrel, a distal tip extending distally from the barrel, and a needle mounted into the distal tip, and
- a safety device as previously described, wherein the ring is mounted around the distal tip of the medical injection device.

Further advantages and advantageous features of the disclosure are disclosed in the following description.

BRIEF DESCRIPTION OF THE DRAWINGS

A possible embodiment of the disclosure will now be described by way of a non-limiting example with reference to the appended figures.

DESCRIPTION OF THE DISCLOSURE

The disclosure relates to a safety device 1 for preventing a user, especially a healthcare professional, from pricking himself or any person around, such as a patient to be treated, with the needle of a medical injection device 100, before or after injection.

Figure 2:
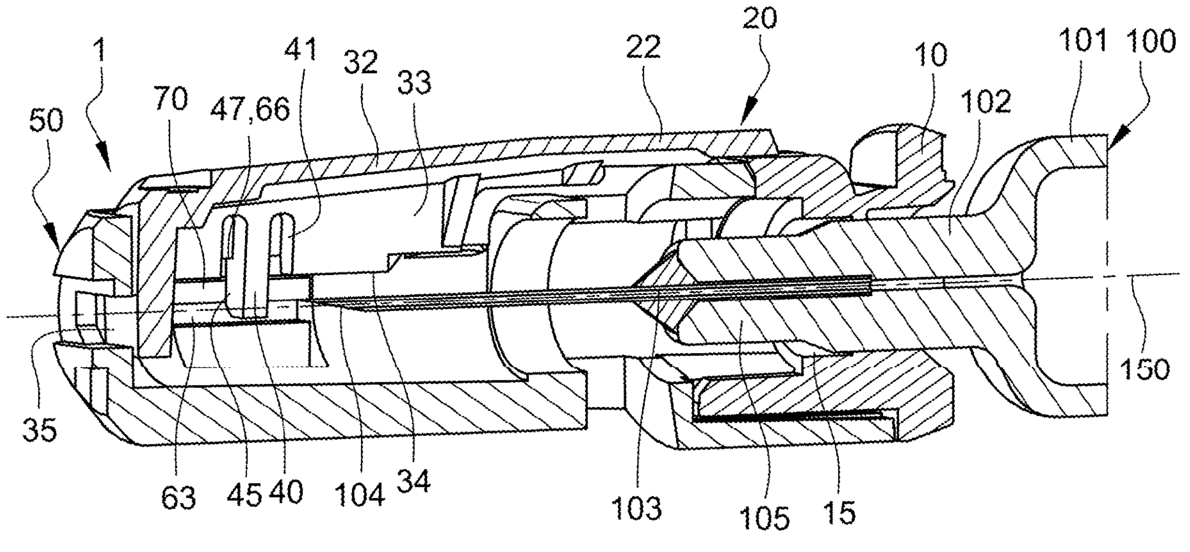
FIG. 2 is a view similar to FIG. 1, showing a longitudinal cross-section of the safety assembly.

As shown in FIG. 2, the medical injection device 100 can be a syringe or the like. The medical injection device 100 comprises a barrel 101, intended to contain a medical composition to be injected to a patient, a distal tip 102 extending distally from the barrel 101 and a needle 103 which is mounted into the distal tip 102 and which has a needle tip 104.

The safety device 1 is configured to be attached to the medical injection device 100, to form a safety assembly 200.

The medical injection device 100, safety device 1 and safety assembly 200 define an axis 150. The terms "axial" and "longitudinal" are used with reference to this axis 150 or to an axis parallel to this axis 150. Furthermore, the distal end of a component must be understood as meaning the end furthest from the hand of the user and the proximal end must be understood as meaning the end closest to the hand of the user, with reference to the axis 150, during the injection process. In other words, the distal direction is the direction of injection and the proximal direction is the opposite direction to said direction of injection.

The term "inner" is used for components located closer to the axis 150 than components described as "outer". The term "inward" refers to a direction oriented towards the axis 150, although not necessarily orthogonal to said axis 150, as opposed to the term "outward".

The term "radial" refers to a direction or a plan orthogonal to axis 150.

Figure 1:
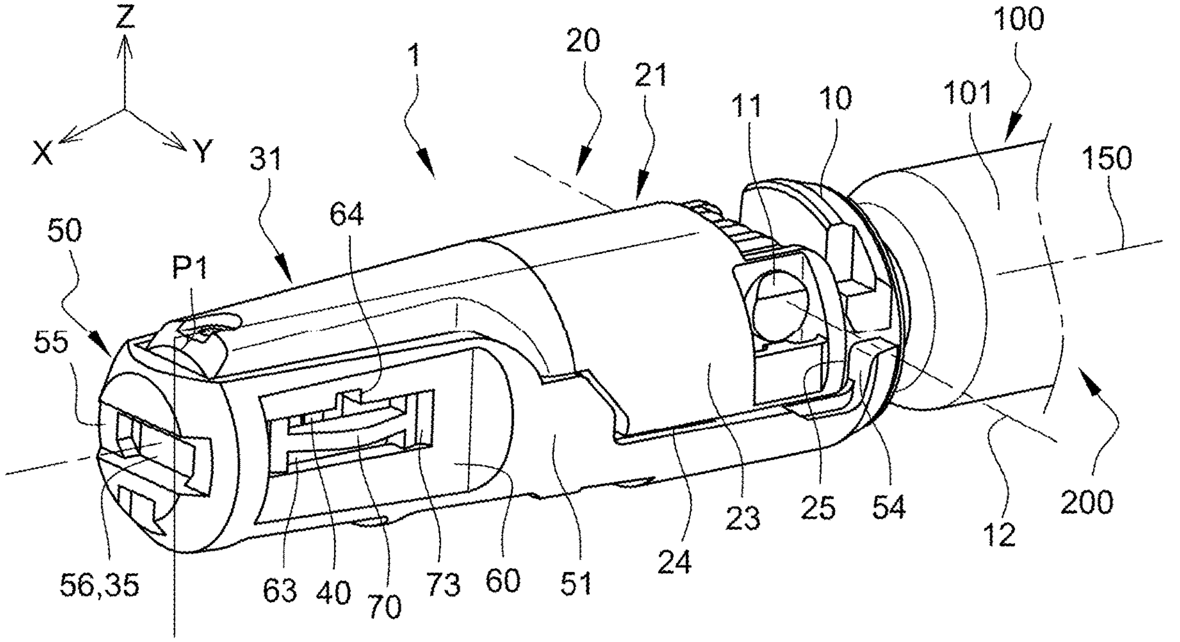
FIG. 1 is a perspective view of a safety assembly according to the disclosure, comprising a safety device mounted on a medical injection device, the safety device being in the storage position and including a protective cap and a protective shield.
Figure 12:
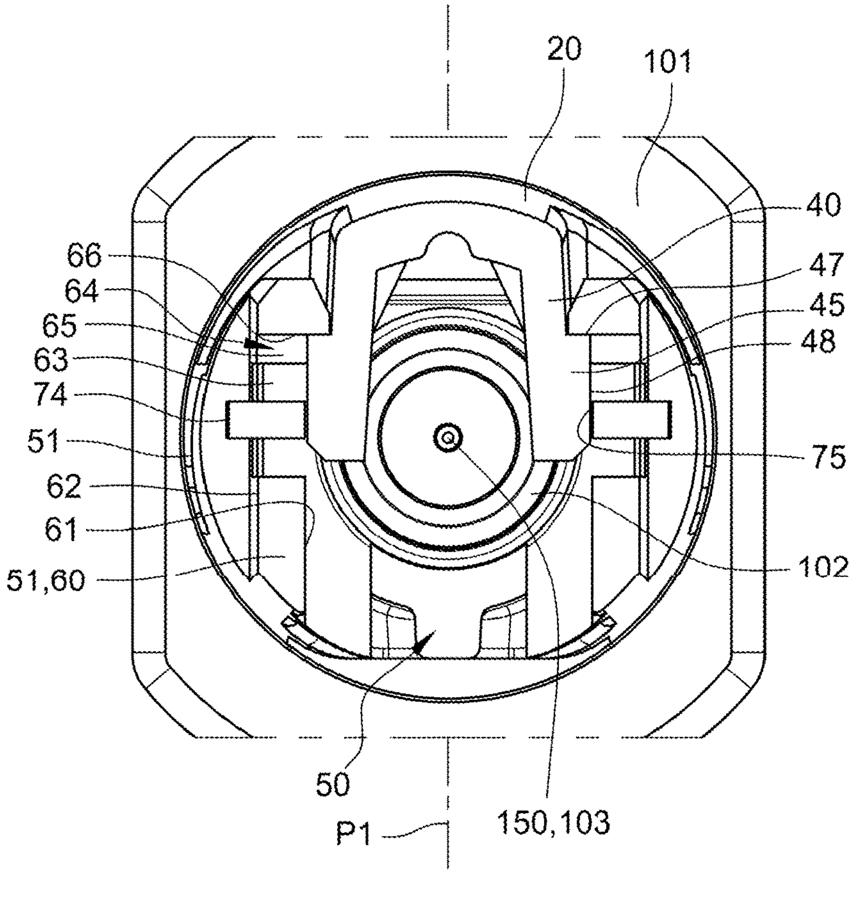
FIG. 12 shows the safety assembly, in the storage position, viewed along the axis and proximally, the safety device being shown in a radial cross-section around the retaining system and the releasing system.

The safety device 1 may comprise a plane of symmetry P1, which contains axis 150 (see FIGS. 1 and 12).

As illustrated in FIG. 1, axis X is defined as being parallel to axis 150, axis Z as being orthogonal to axis X and included in plane P1, and axis Y as being orthogonal to both axes X and Z.

The safety device 1 comprises a ring 10 which is mounted around and attached to the distal tip 102. Alternatively, the ring could be made as a single part with the distal tip 102.

The ring 10 has a substantially cylindrical shape and a central through hole 15 which is adapted to receive the distal tip 102 of the medical injection device 100, as illustrated in FIG. 2. In the mounted position, the distal tip 102 extends distally beyond the ring 10; in other words, an end portion 105 of the distal tip 102 protrudes distally from the ring 10.

The ring 10 may further have a first hinge portion 11, the function of which will be described below. The first hinge portion 11 may comprise, on each side of plane P1, an outwardly extending pin. The pins together form a pivot axis 12 which is orthogonal to plane P1.

The safety device 1 further comprises a protective shield 20 configured to act as a physical barrier for preventing needle stick injury with the needle 103, before and after the injection process. To that end, the safety device 1 is movably coupled to the ring 10, and configured to adopt successively:

- a storage position wherein the protective shield 20 covers the needle tip 104 (FIGS. 1 and 2 for instance);
- an operative position wherein the protective shield 20 uncovers the needle tip 104, to allow performing the injection (FIG. 3);
- and a safety position wherein the protective shield 20 covers the needle tip 104.

In the illustrated embodiment, the movement of the protective shield 20 from its storage position to its operative position is a pivoting movement, but this should not be considered as limitative.

Figure 7:
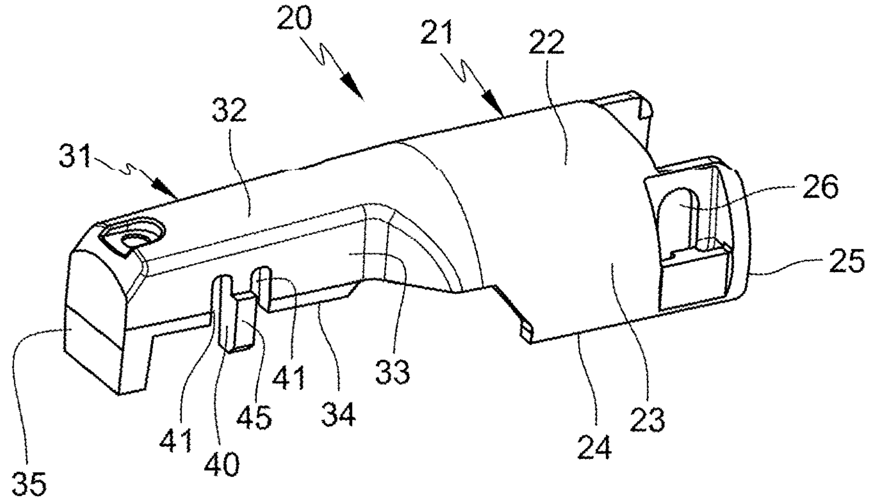
FIG. 7 is a perspective view of the protective shield.
Figure 8:
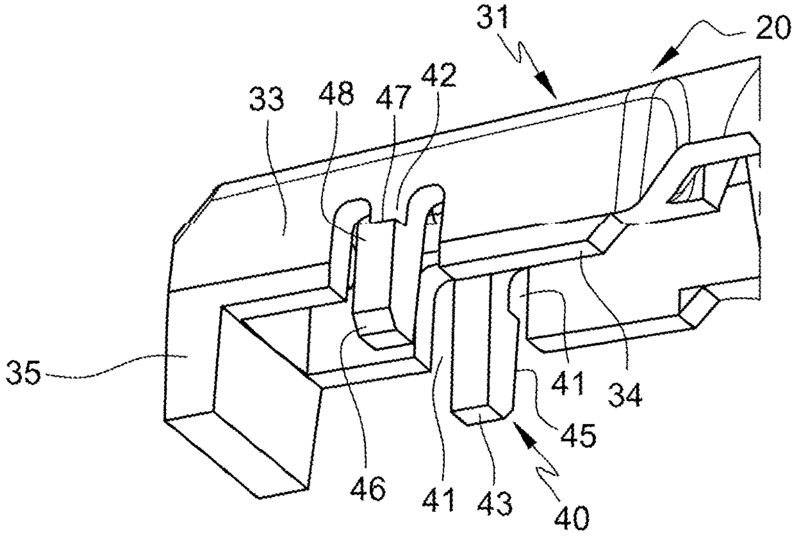
FIG. 8 is a partial perspective view of the protective shield, viewed from a different direction.
Figure 9:
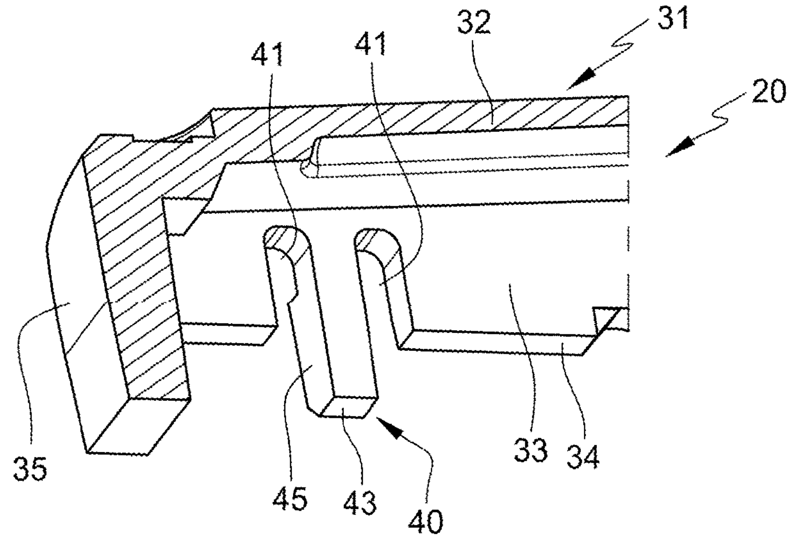
FIG. 9 is a partial perspective view of the protective shield, showing a longitudinal cross-section thereof.

With reference to FIGS. 7 to 9, the protective shield 20 comprises a proximal portion 21 and a distal arm 31 that extends distally from the proximal portion 21.

The proximal portion 21 has a generally semi cylindrical shape with one central portion 22 and two side flanges 23 that project from the central portion 22, the side flanges 23 being located on either side of plane P1 and facing each other. Each flange 23 has a longitudinal edge 24 and a proximal edge 25. In each flange 23 is provided a hole 26 intended to receive one pin of the ring 10. The holes 26 thus form a second hinge portion pivotally coupled to the first hinge portion provided on the ring 10, to allow pivoting movement of the protective shield 20 with respect to the ring 10 about axis 12. The flanges 23 extend globally parallel to plane P1—although they may be slightly curved around a longitudinal axis—while, in the storage position, the central portion 22 extends globally orthogonally to axis Z—although it may be slightly curved around a longitudinal axis.

The distal arm 31 has a generally U-shaped cross section including one central portion 32 and two side panels 33 that project from the central portion 32, the side panels 33 being located on either side of plane P1 and facing each other. Each side panel 33 has a longitudinal edge 34. The distal arm 31 further comprises a distal radial wall 35. The side panels 33 extend globally parallel to plane P1—and are preferably substantially plat—while the central portion 32 extend globally orthogonally to axis Z—although it may be slightly curved around a longitudinal axis.

Along axis Y, the distance between the two side panels 33 is smaller than the distance between the two side flanges 23. Along axis Z, in the storage position, the distance between the central portion 32 and the longitudinal edge 34—in other words the height of the side panel 33—is smaller than the distance between the central portion 22 and the longitudinal edge 24—in other words the height of the flange 23. Besides, along axis Z, in the storage position, the height of the distal radial wall 35 is greater than the height of the side panels 33.

Each of the side panels 33 comprises a leg 40 which extends away from the central portion 32. The leg 40 may be formed between two parallel slots 41 formed in the side panel 33. The slots 41, and thus the leg 40, may extend along axis Z, in the storage position. The leg 40 extends from its base 42, by which it is connected to the side panel 33, towards its free end 43 which is preferably located further from the central portion 32 than the longitudinal edge 34 of the side panel 33. The leg 40 has a protrusion 45 which extends outwardly. As best seen in FIG. 8, the protrusion 45 has:

- an end face 46, which may be located close to or level with the leg free end 43, and which preferably forms a slope;
- an abutment face 47, which is opposite the end face 46, and which is preferably oriented substantially orthogonal to axis Z, in the storage position;
- and an activation face 48, which forms the outer face of the protrusion 45. Along axis Y, the activation face 48 is preferably located further from axis 150 than the side panel 33, and closer to said axis 150 than the flange 23. The activation face 48 may be substantially flat and parallel to plane P1.

In the figures, the leg 40 is shown in a first state, in which it is substantially parallel to plane P1. From this first state, owing to the slots 41, the leg 40 can be elastically moved, deflected or deformed towards the inside of the safety device 1 towards a second state, as will be described.

The safety device 1 also comprises a protective cap 50 which is mounted on the ring 10 in a storage position so as to cover at least the needle tip 104 and which can be separated from the ring 10 prior to the use of the medical injection device 100.

With reference to FIGS. 2 and 4 to 6, the protective cap 50 comprises a substantially tubular body in which the needle 103 is housed in the storage position. The substantially tubular body has a peripheral wall 51 which is included in a generally cylindrical envelope.

In the proximal portion 52 of the protective cap 50, the peripheral wall 51 is inwardly recessed with respect to the cylindrical envelope, so as to form a semi cylindrical housing for receiving the proximal portion 21 of the protective shield 20 such that, in the storage position, said proximal portion 21 is located inside the cylindrical envelope.

The protective cap 50 may comprise two side pegs 53 extending proximally from the proximal end of the protective cap 50. The distal face 54 of the pegs 53 may be concavely curved.

Besides, the protective cap 50 may have a distal radial wall 55 provided with a hole 56.

In its distal portion 57, the protective cap 50 can have a distal radial opening 58 which may be configured to receive the distal arm 31 of the protective shield 20. To that end, preferably, the distal radial opening 58 is elongated along axis 150, and has a dimension along axis Y which is substantially identical—or slightly greater, to provide an appropriate fitting clearance—to the distance between the outer faces of the side panels 33, along axis Y, as best seen in FIG. 12.

In the distal portion 57 of the protective cap 50, on both sides of plane P1, the peripheral wall 51 has an inwardly recessed portion 60 having an inner face 61 and an outer face 62 which can be substantially parallel to P1, as shown in FIG. 12 for instance.

In the recessed portion 60 is arranged a window 63, which may be substantially rectangular and elongated along axis 150. Furthermore, the protective cap 50 comprises a cavity 64 which opens towards the inside of the safety device 1. The cavity 64 may be arranged in the recessed portion 60. It may extend through the peripheral wall 51, i.e. also open towards the outside of the safety device 1. The cavity 64 may further open into the window 63. In the illustrated embodiment, the cavity 64 is located closer to the distal arm 31 of the protective shield 20 than the window 63, in the storage position. The cavity 64 may have opposite faces 65 orthogonal to axis 150, and a face 66 orthogonal to axis Z which forms a shoulder.

The protective cap 50 comprises a trigger 70 which is housed in the window 63. The trigger 70 may have a H shape including a central rod 71, which preferably extends parallel to axis 150, and two branches 72 on either part of the central rod 71. Each branch 72 may be adjacent an edge 67 of the window 63 and hingedly connected to said edge 67. In an embodiment, the trigger 70 is made as a single piece with the protective cap 50, and a portion 73 of reduced thickness forms the hinge between the trigger 70 and the window edge 67.

The trigger 70 may have a projection 74 which extends outwardly from the recessed portion outer face 62 but not beyond the cylindrical envelope of the protective cap 50, in the radial direction. Besides, the trigger 70 may have an inner face 75 which is substantially level with the recessed portion inner face 61.

The trigger 70 is configured to be elastically moved, deflected or deformed towards the inside of the safety device 1 by a manual inward pressure exerted on said trigger 70. This may result from the hinge 73 which is formed by a portion of reduced thickness and which connects the trigger 70 to the tubular body of the protective cap 50.

Each of the ring 10, protective shield 20 and protective cap 50 is preferably made of any rigid polymer adapted to medical use, such as high-density polyethylene (PE), polypropylene (PP), polycarbonate (PC), acrylonitrile butadiene e styrene (ABS), polyoxymethylene (POM), polystyrene (PS), polybutylene terephthalate (PBT), polyamide (PA), and their combinations.

In the storage position, as shown in FIGS. 1, 2, and 10-12, the protective cap 50 is mounted on the ring 10 so as to cover the needle 103 up to the needle tip 104 and preferably beyond, in the distal direction.

Figure 3:
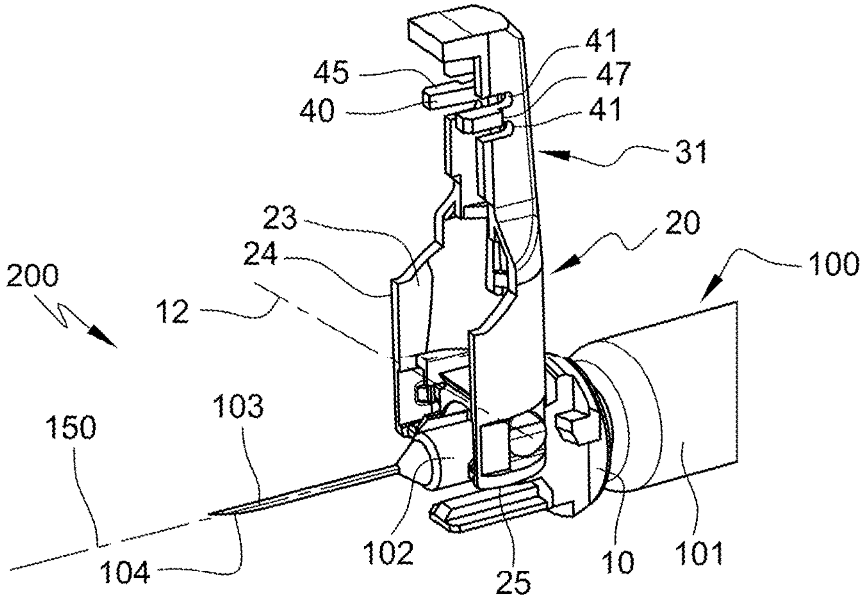
FIG. 3 is a perspective view of the safety assembly, with the protective shield removed and the protective cap in the operative position.
Figure 4:
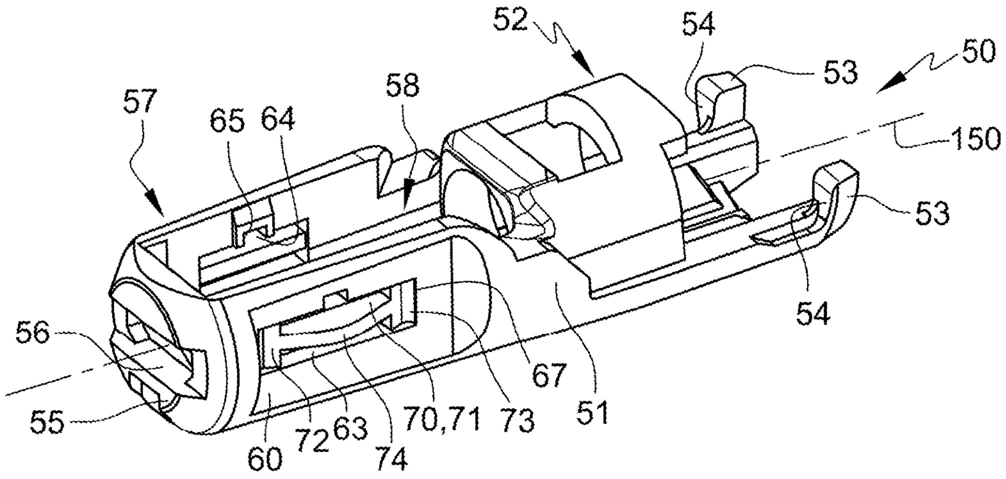
FIG. 4 is a perspective view of the protective cap.
Figure 5:
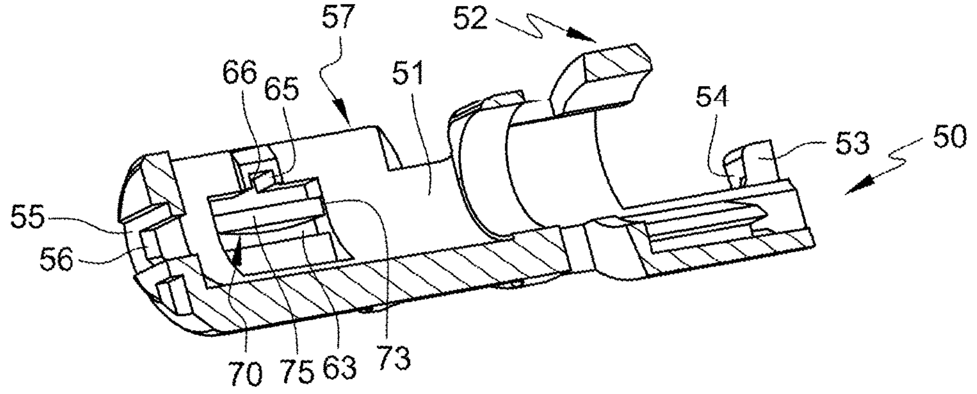
FIG. 5 is a perspective view of the protective cap, showing a longitudinal cross-section thereof.
Figure 6:
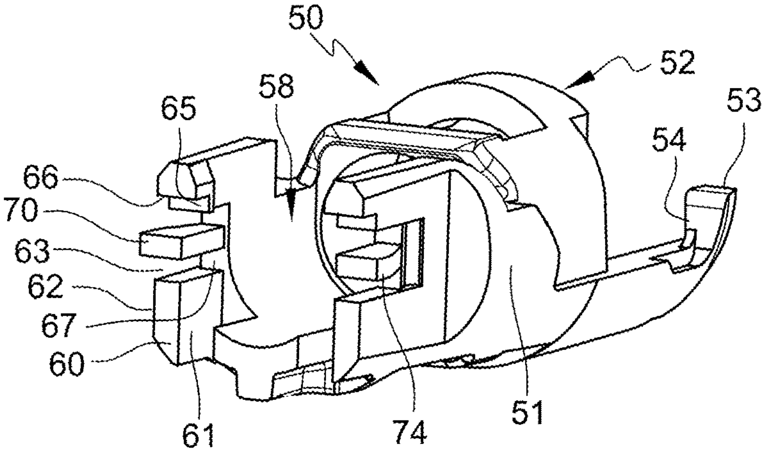
FIG. 6 is a perspective view of the protective cap, showing a radial cross-section thereof.

The protective shield 20 is mounted on the ring 10, with the first hinge portions 11—such as the pins—engaged in the respective holes 26, so that the protective shield 20 can rotate about pivot axis 12 towards its operative position, illustrated in FIG. 3. In the storage position, the distal arm 31 may extend substantially parallel to axis 150, while in the operative positon, the distal arm 31 may extend substantially parallel to axis Z.

The protective shield 20 further cooperates with the protective cap 50. More specifically, the distal arm 31 is at least partially housed in the distal radial opening 58 of the protective cap 50 as previously explained. Alternatively, the distal arm 31 may only radially face said distal radial opening 58 without being received in it. Then, the distal radial wall 35 of the distal arm 31 may be located adjacent the distal radial wall 55 of the protective cap 50, inside the safety device 1, so as to close the hole 56. The proximal portion 21 of the protective shield 20 may also be arranged such that the proximal edge 25 of each side flange 23 is adjacent the distal face 54 of the pegs 53 of the protective cap 50.

Figure 10:
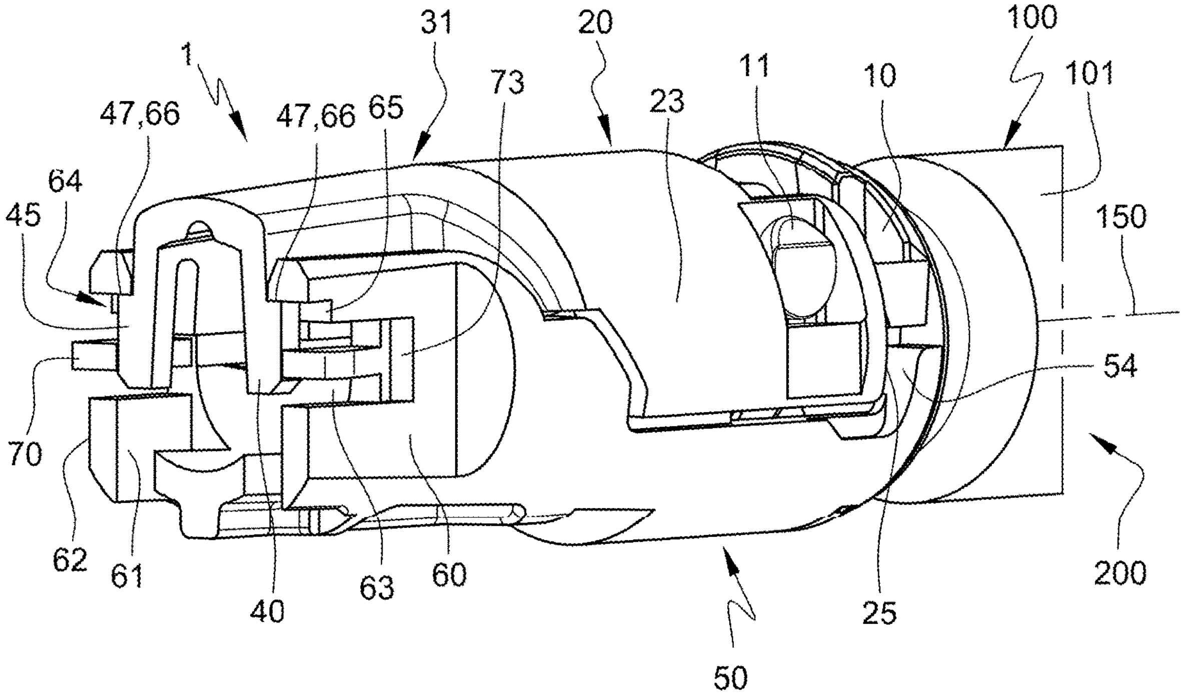
FIG. 10 is a perspective view of the safety assembly, in the storage position, showing a radial cross-section thereof around the retaining system and the releasing system.
Figure 11:
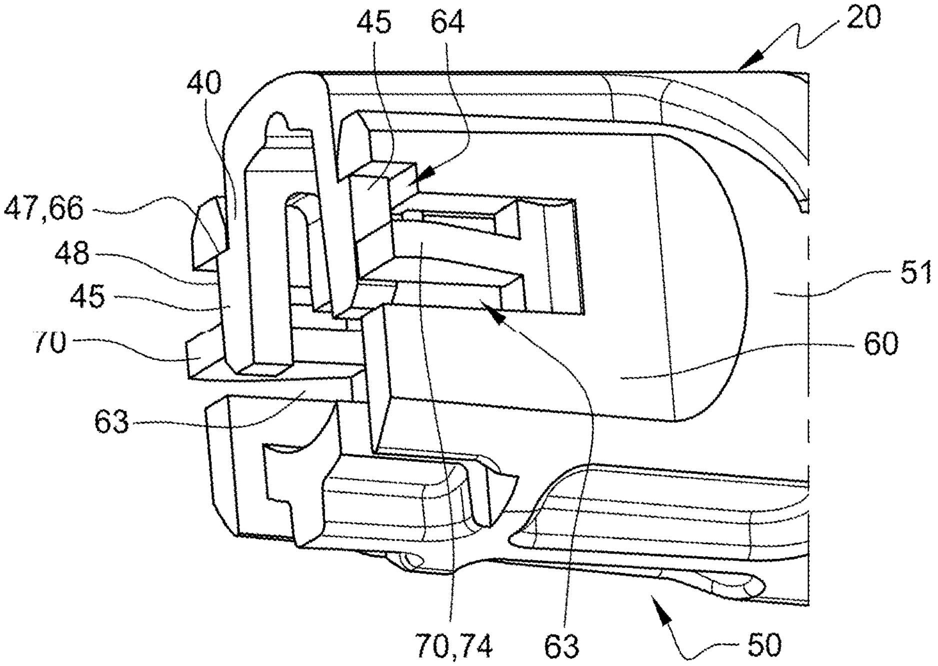
FIG. 11 is a partial view similar to FIG. 10, viewed from a different direction.

In the storage position, as best seen in FIGS. 10, 11 and 12, on each side of plane P1, the leg 40 of the protective shield 20 extends towards the inside of the safety device 1. The leg 40 is engaged in the cavity 64 with the abutment face 47 of the protrusion 45 being in contact with, or very close to, the face 66 of the cavity 64. Thus, the abutment face 47 forms a first retaining portion and the face or shoulder 66 forms a second retaining portion of a retaining system. Owing to the cooperation between the first and second retaining portions 47, 66 in the storage position, the retaining system prevents the protective shield 20 from moving to its operative position.

The leg 40 is further located between the opposite faces 65 of the cavity 64. Providing no or only a small gap between the leg 40 and said faces 65 also prevents any relative axial movement between the protective cap 50 and the protective shield 20.

Moreover, in the storage position, a portion of the leg 40 faces a portion of the trigger 70 in the radial direction. More specifically, the activation face 48, i.e. the outer face of the protrusion 45 arranged on the leg 40, is in contact with or in close proximity to the inner face 75 of the central rod 71 of the trigger 70.

When a user wants to use the medical injection device 100, he first has to remove the protective cap 50. To that end, the user has to exert an inward pressure on the trigger 70, for example on the projection 74 of the central rod 71, typically by pressing the protective cap 50 between his thumbs. As a result, the trigger 70 is elastically moved, deflected or deformed inwards. Owing to the cooperation between the activation face 48 of the leg 40 and the inner face 75 of the trigger 70, the trigger 70 in turn causes the leg 40 to be elastically moved, deflected or deformed inwards, until the abutment face 47 of the protrusion 45 of the leg 40 disengages from the shoulder 66 of the cavity 64.

In other words, the trigger 70 forms part of a releasing system which can be activated by a manual inward pressure and which allows releasing the retaining system.

Thus, both the releasing system (in particular the trigger 70) and the retaining system (in particular the shoulder 66 and abutment face 47) change from a first state, in which the protective shield 20 is maintained in the storage position, towards a second state, in which the protective shield 20 is free to move towards its operative position.

The user can then pull the protective cap 50 distally away from the ring 10. During this pulling movement, the distal face 54 of the pegs 53 of the protective cap 50 may cooperate with the proximal edge 25 of the side flanges 23 of the protective shield 20 as cam surfaces to automatically cause the rotation of the protective shield 20 from its storage position to its operative position.

In the operative position, illustrated in FIG. 3, the needle 103 is no more covered by the protective cap 50 nor by the protective shield 20, and injection can be performed.

Once the injection is completed, the user can move the protective shield 20 to a safety position in which it covers the needle tip 104. The safety position can be identical to the storage position. Alternatively, in the safety position, the protective shield 20 may be closer to the needle 103 than in the storage position. In any event, the safety position ensures no needle stick injury can occur.

Further advantages of the disclosure are listed below:
- the safety device does not require a triggering step in order to expose the needle tip before use, and therefore allows improving the pace of the medical act and increasing the safety level of the medical device;
- the safety device has a diameter no greater than the syringe barrel and a limited length. As a consequence, it can be accommodated in a standard packaging used for prefillable syringes;
- the safety device allows a complete exposure of the needle tip and does not impede the medical act as it provides direct view and access to the needle tip.

It is to be understood that the present disclosure is not limited to the embodiments described above and illustrated in the drawings; rather, the skilled person will recognize that many changes and modifications may be made within the scope of the appended claims.

The invention claimed is:

1. A safety device for preventing needle stick injury with a needle extending from a distal tip of a medical injection device, comprising:
- a ring configured to be attached to the distal tip of the medical injection device;
- a protective shield movably coupled to the ring, the protective shield being configured to adopt successively a storage position wherein the protective shield covers the needle tip, an operative position wherein the protective shield uncovers the needle tip and a safety position wherein the protective shield covers the needle tip;
- a protective cap which is mounted on the ring in a storage position so as to cover at least the needle tip, and which can be separated from the ring prior to the use of the medical injection device;
- a retaining system comprising a first retaining portion arranged on the protective shield and a second retaining portion arranged on the protective cap, wherein the first and second retaining portions cooperate in the storage position to prevent the protective shield from moving to its operative position;

wherein the safety device further comprises a releasing system for releasing the retaining system, the releasing system being configured to be activated by a manual inward pressure exerted on the protective cap.

2. The safety device according to claim 1, wherein the releasing system is arranged on the protective cap.

3. The safety device according to claim 1, wherein, in the storage position, the releasing system substantially faces at least a part of the retaining system in the radial direction.

4. The safety device according to claim 1, wherein, in the storage position, the releasing system is in contact with or in close proximity to at least a part of the retaining system, the releasing system being preferably configured to directly release the retaining system when activated.

5. The safety device according to claim 1, wherein the protective cap comprises a substantially tubular body having a distal radial opening and the protective shield has a distal arm which, in the storage position, is housed in or radially faces the distal radial opening of the protective cap, wherein the first retaining portion is arranged on at least one of the two longitudinal sides of the distal arm of the protective shield and the second retaining portion is arranged on a portion of the substantially tubular body peripheral wall adjacent the distal radial opening.

6. The safety device according to claim 1, wherein the retaining system and/or the releasing system comprise(s) at least one element which is configured to be elastically moved, deflected or deformed from a first state, in which the protective shield is maintained in the storage position, towards a second state, in which the protective shield is free to move towards its operative position.

7. The safety device according to claim 1, wherein the protective shield comprises at least one leg extending towards the inside of the safety device, the leg having a protrusion which extends outwardly and which has an abutment face forming the first retaining portion.

8. The safety device according to claim 7, wherein the leg of the protective shield is configured to be elastically moved, deflected or deformed towards the inside of the safety device upon activation of the releasing system, to disengage from the shoulder of the protective cap.

9. The safety device according to claim 1, wherein the protective cap comprises at least one cavity which opens at least towards the inside of the safety device, one face of said cavity being a shoulder forming the second retaining portion.

10. The safety device according to claim 9, wherein the cavity further opens into the window.

11. The safety device according to claim 1, wherein the releasing system comprises at least one trigger which is housed in a window arranged in a peripheral wall of the protective cap, the trigger being hingedly connected to at least one edge of the window and being configured to be elastically moved, deflected or deformed towards the inside of the safety device by a manual inward pressure exerted on said trigger.

12. The safety device according to claim 11, wherein the trigger has a H shape with a central rod on which a manual inward pressure can be exerted and two branches on either part of the central rod, each branch being adjacent an edge of the window and hingedly connected to said edge.

13. The safety device according to claim 11, wherein the trigger is made as a single piece with the protective cap, and wherein a portion of reduced thickness forms a hinge between the trigger and the window edge.

14. The safety device according to claim 11, wherein the window is arranged in an inwardly recessed portion of the peripheral wall of the protective cap.

15. The safety device according to claim 14, wherein said recessed portion has an inner face and an outer face, the trigger having:

a projection which extends outwardly from the recessed portion outer face but not beyond a cylindrical envelope of the protective cap-(50), in the radial direction;

and/or an inner face which is substantially level with the recessed portion inner face.

16. The safety device according to claim 1, wherein the ring has a first hinge portion and the protective shield has a second hinge portion pivotally coupled to the first hinge portion, whereby the movement of the protective shield from its storage position to its operative position is a pivoting movement.

17. The safety device according to claim 1, wherein the protective cap and the protective shield have cooperating actuation surfaces configured so that a distal movement of the protective cap away from the ring automatically entails a movement of the protective shield from its storage position to its operative position.

18. A safety assembly, comprising:

a medical injection device comprising a barrel, a distal tip extending distally from the barrel, and a needle mounted into the distal tip, and a safety device according to claim 1, wherein the ring is mounted around the distal tip of the medical injection device.

* * * * *